United States Patent [19]

Lansbarkis et al.

[11] Patent Number: 5,476,985

[45] Date of Patent: Dec. 19, 1995

[54] PROCESS FOR SEPARATING LINEAR AND BRANCHED HYDROCARBONS USING ALKYLENE-BRIDGED POLYSILSESQUIOXANES

[75] Inventors: James R. Lansbarkis, El Dorado, Calif.; Timothy A. Brandvold, Buffalo Grove, Ill.

[73] Assignee: UOP, Des Plaines, Ill.

[21] Appl. No.: 357,901

[22] Filed: Dec. 16, 1994

[51] Int. Cl.$^6$ .................................................. C07C 7/12
[52] U.S. Cl. .............................. 585/825; 585/826; 585/830
[58] Field of Search .................................. 585/825, 826, 585/830

[56] References Cited

U.S. PATENT DOCUMENTS

| | | | |
|---|---|---|---|
| 2,985,589 | 5/1961 | Broughton et al. | 210/34 |
| 4,061,724 | 12/1977 | Grose et al. | 423/335 |
| 4,309,281 | 1/1982 | Dessau | 208/310 Z |
| 4,455,444 | 6/1984 | Kulprathipanja et al. | 585/826 |
| 4,486,618 | 12/1984 | Kulprathipanja et al. | 585/829 |
| 4,992,618 | 2/1991 | Kulprathipanja | 585/820 |
| 5,396,020 | 3/1995 | Lansbarkis | 585/825 |
| 5,414,192 | 5/1995 | Lansbarkis | 585/825 |

OTHER PUBLICATIONS

Shea, K. J., Loy, D. A., *Chemistry of Materials*, 1989, 1, pp. 572–574.

Shea, K. J., Loy, D. A., Webster, O., *J. Am. Chem. Soc.*, 1992, pp. 6700–6710.

Shea, K. J., Loy, D. A., Webster, O., *Mater. Res. Soc, Symp. Proc.*, 1990, 180, pp. 975–980.

Shea, K. J., Loy, D. A., Webster, O., *Polym. Mater. Sci. Eng.*, 1990, 63, pp. 281–285.

Oviatt, H. W., Shea, K. J., Small, J. H., *Chem. Mater.*, 1993, 5, pp. 943–950.

Small, J. H., Shea, K. J., Loy, D. A., *J. Non-Crystalline Solids*, 1993, 160, pp. 234–246.

*Primary Examiner*—Asok Pal
*Assistant Examiner*—Nhat D. Phan
*Attorney, Agent, or Firm*—Thomas K. McBride; Eugene I. Snyder

[57] ABSTRACT

An adsorptive process to separate the components of a solution of linear and branched hydrocarbons into a linear hydrocarbon portion and a branched hydrocarbon portion where the adsorbent is an alkylene-bridged polysilsesquioxane has been developed. The hydrocarbon components to be separated may be alkanes, alkenes, or alkynes, and the alkylene-bridging group of the adsorbent may contain from about 2 to about 14 carbon atoms. A specific embodiment of the invention is one where the process is operated in the simulated moving bed mode.

9 Claims, 3 Drawing Sheets

PROCESS FOR SEPARATING LINEAR AND BRANCHED HYDROCARBONS USING ALKYLENE-BRIDGED POLYSILSESQUIOXANES

BACKGROUND OF THE INVENTION

Processes to separate alkane or alkene mixtures into their linear and branched component portions are an important necessity in industry. These separation processes generally use a solid adsorbent to selectively adsorb desired components from the mixture. The components are later desorbed and recovered. Typically the solid adsorbents used in industry are zeolites or other molecular sieve materials, and a wide variety of such adsorbents have been disclosed in the prior art. For example, the preferential adsorption of linear alkenes over branched alkenes using adsorbents such as ZSM-5 and silicalite was disclosed in U.S. Pat. Nos. 4,309,281 and 4,061,724, respectively. The crystalline molecular sieve silicalite was also used in U.S. Pat. No. 4,486,618 to separate linear alkenes having six carbon atoms from branched and cyclic alkenes having six carbon atoms and in U.S. Pat. No. 4,455,444 to perform the similar separation of linear alkanes having six carbon atoms from branched and cyclic alkanes having six carbon atoms. U.S. Pat. No. 4,992,618 disclosed the use of the commercially available type 5A molecular sieve to separate linear alkanes from non-linear alkanes.

The present invention expands the range of useful solid adsorbents to effect the separation of hydrocarbons according to whether components are branched or linear to include alkylene-bridged polysilsesquioxanes. Specific organically-bridged polysilsesquioxane materials and their preparation have been disclosed in Shea, K. J., Loy, D. A. *Chem. Mater.* 1989, 1, pp. 572–574; Shea, K. J., Loy, D. A., Webster, O. *J. Am. Chem. Soc.* 1992, 114, pp. 6700–6710; Shea, K. J., Loy, D. A., Webster, O. *Mater. Res. Soc. Symp. Proc.* 1990, 180, pp. 975–980; Shea, K. J., Loy, D. A., Webster, O. *Polym. Mater. Sci. Eng.* 1990, 63, pp. 281–285. Specific alkylene-bridged polysilsesquioxanes and their preparation have been disclosed in Oviatt, H. W., Shea, K. J., Small, J. H. *Chem. Mater.* 1993, 5, pp. 943–950 and Small, J. H., Shea, K. J., Loy, D. A. *J. Non-Crystalline Solids* 1993, 160, pp. 234–246. This art teaches that organic groups can be introduced at regular intervals in an inorganic silicate framework, thus forming a three-dimensional organic-inorganic hybrid silicate-like polymeric material, also called an organically-bridged polysilsesquioxane. A two-dimensional representation of the well-known inorganic silicate framework is shown in I, and an analogous representation of the organically-bridged polysilsesquioxane where the ⋮⋮⋮ represents the organic bridging group is shown in II. Of course, frameworks I and II, in reality, extend to form a three-dimensional, continuous, amorphous solid.

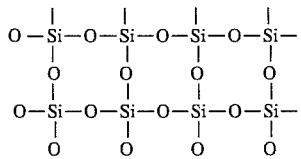

I

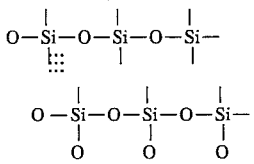

II

The specific organic bridging groups disclosed in the art include ethylene, tetramethylene, hexamethylene, octamethylene, decamethylene, and tetradecamethylene. In view of the prior art, alkylene-bridging groups of trimethylene, pentamethylene, heptamethylene, nonamethylene, undecamethylene, dodecamethylene, tridecamethylene and their preparation are readily apparent to those skilled in the art. Organically-bridged polysilsesquioxanes containing these bridging groups are termed alkylene-bridged polysilsesquioxanes. One stated objective of the disclosed work was to provide molecular level control of the morphology of the framework, another was to provide a new chromatographic support, and a third was use in optical applications. However, applicant has found that these materials perform as adsorbents for linear and branched alkanes, alkenes, and alkynes at low temperatures. Furthermore, applicant has discovered that the adsorbed branched hydrocarbons may be desorbed from the alkylene-bridged polysilsesquioxanes using environmentally preferred alkane desorbents.

SUMMARY OF THE INVENTION

The purpose of the invention is to provide an adsorptive process to separate the components of a solution of linear and branched hydrocarbons into a linear hydrocarbon portion and a branched hydrocarbon portion where the adsorbent is an alkylene-bridged polysilsesquioxane. The hydrocarbons may be alkanes, alkenes, or alkynes and the alkylene bridging group may contain from about 2 to about 14 carbon atoms. A specific embodiment of the invention is one where the process is operated in the simulated moving bed mode.

DETAILED DESCRIPTION OF THE INVENTION

Figure 1:
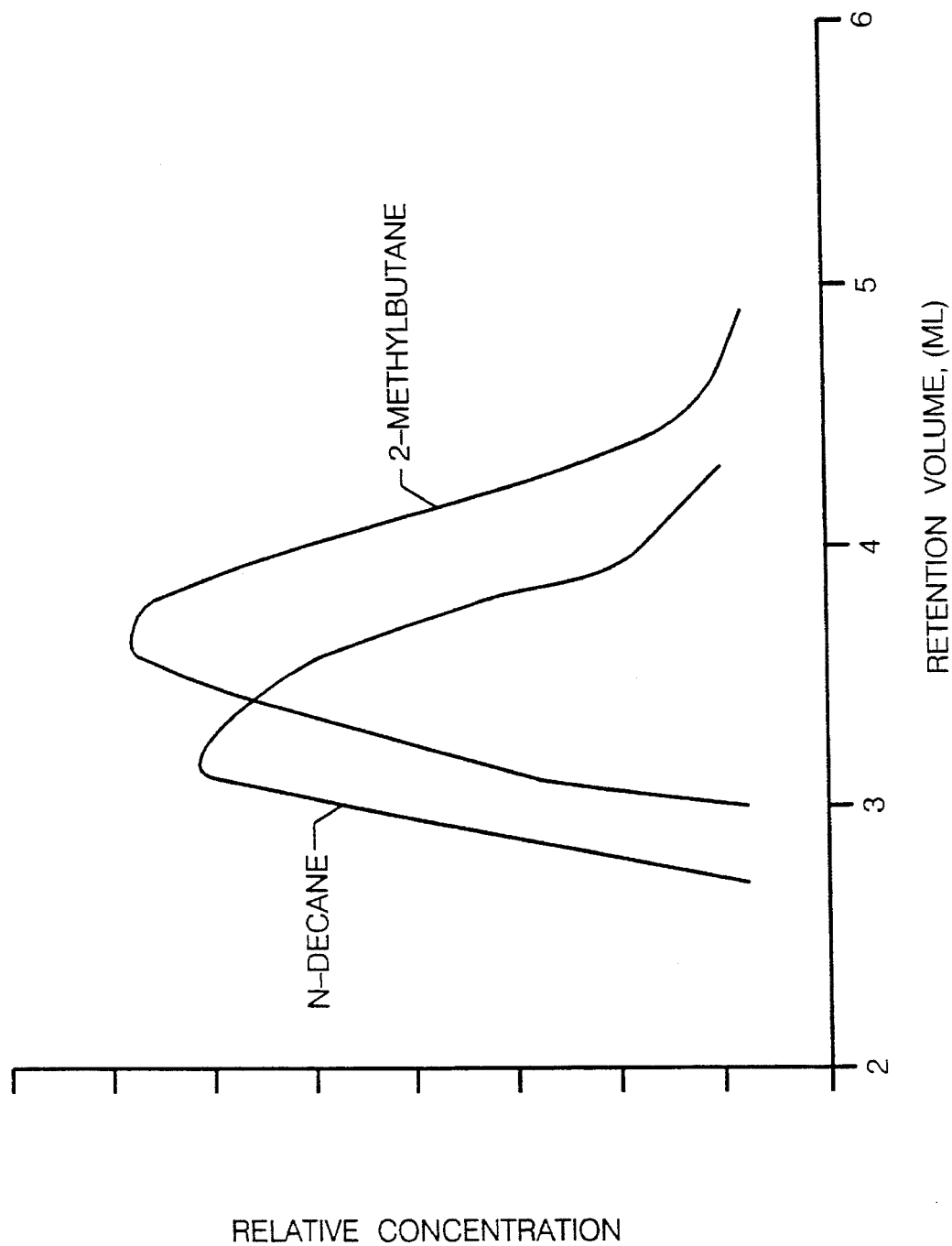
FIG. 1 is the chromatographic plot of the separation of a mixture of a linear alkane and a branched alkane using ethylene-bridged polysilsesquioxane as the adsorbent as conducted in Example 1.

The subject inventive process of separating a solution of linear and branched hydrocarbons into a linear hydrocarbon portion and a branched hydrocarbon portion is accomplished by utilizing the surprising adsorptive properties of alkylene-bridged polysilsesquioxanes, specifically where the alkylene-bridging group contains from about 2 to about 14 carbon atoms. Surprisingly, the alkylene-bridged polysilsesquioxane adsorbents perform best when the process is operated at low temperatures, typically, from about 30° to about 80° C. as compared to the zeolitic and molecular sieve adsorbents currently used in industry which perform optimally at about 100° to about 200° C. Lower operating temperatures provide advantages such as reduced utility costs and decreased undesired reactivity among the components of the solution to be separated. Furthermore, when operating in the liquid phase, alkanes may be employed as desorbents, allowing the present invention to be more environmentally responsible than other liquid phase separation processes which require alkene desorbents.

The invention is best performed when only one class of hydrocarbons is present in the solution to be separated. Consequently, the preferred embodiments of the invention are the separation of a solution of linear and branched alkanes into a linear alkane portion and a branched alkane portion, the separation of a solution of linear and branched alkenes into a linear alkene portion and a branched alkene portion, and the separation of a solution of linear and branched alkynes into a linear alkyne portion and a branched alkyne portion. The most preferred embodiment is the one where the hydrocarbons are alkanes. In general terms for the alkane separation, the solution would be contacted with the alkylene-bridged polysilsesquioxane adsorbent, which would adsorb the hydrocarbons with increasing strength in the order of linear hydrocarbons< branched hydrocarbons. The desorbent would be added to the system, and the weakly adsorbed linear alkanes would be desorbed, removed from the system, and collected. The more strongly adsorbed branched alkanes then would be desorbed by the desorbent, removed from the system, and collected. The linear alkanes and the branched alkanes could then be separately recovered from excess desorbent using a technique such as fractional distillation. Similarly, the alkene and alkyne separations would proceed in the same manner as discussed above.

The alkylene-bridged polysilsesquioxane adsorbent may be used in any of the commonly known solid adsorbent systems such as fixed bed, moving bed, and simulated moving bed. In a fixed bed system, increments of the solution to be separated and desorbent are contacted alternately with the adsorbent which is stationary. As the solution components move through the bed, they gradually separate into bands. The bands travel at different rates corresponding to how strongly the components are retained by the adsorbent. As the separated bands elute from the bed, they are collected. Since different bands elute sequentially, the process is semicontinuous. The size of the fixed bed system may vary from a commercial scale system to an analytical scale system, depending upon the application. In a moving bed process, the adsorbent is physically conveyed through the system counter to the continuously introduced fluid streams. While it is possible to use the alkylene-bridged polysilsesquioxane adsorbent in the moving bed system, it is the least preferred due to typical problems caused by the physical movement of the solid such as attrition and maintaining a uniform flow. Additional information regarding fixed bed and moving bed systems may be found in Mowry, J. R. In *Handbook of Petroleum Refining Processes;* Meyers, R. A., Ed.; McGraw-Hill Book Company: New York, 1986, Chapter 8.8.

The preferred operation of the invention is in a simulated moving bed system as described in U.S. Pat. No. 2,985,589. As with the moving bed, in the simulated moving bed system, the solution to be separated and the desorbent are continuously fed to the system and adsorption and desorption are continuously taking place producing an extract stream and a raffinate stream. The weakly adsorbed portion of the solution, the linear alkane, alkene or alkyne portion, travels with the fluid flow of the system, is removed from the system in the raffinate stream, and collected. The strongly adsorbed portion of the solution, the branched alkane, alkene or alkyne portion, is carried with the simulated movement of the adsorbent, desorbed from the adsorbent by the desorbent, removed from the system in the extract stream, and collected. The raffinate stream and the extract stream, in addition to containing their respective hydrocarbon portion, also contain desorbent. At a point after the separation, the hydrocarbons may be recovered from the desorbent using conventional means such as fractional distillation.

The adsorbent is usually a succession of sub-beds which can be housed in one chamber, or in two or more chambers, and different applications may require differing numbers of sub-beds. The shift in the locations of the inputs and outputs in the direction of the fluid flow through the bed simulates the movement of the solid adsorbent in the opposite direction. The system may also be used where the simulated movement of the adsorbent bed is cocurrent with the direction of the fluid flow. Commercially, moving the locations of the inputs and outputs is accomplished by a fluid directing device known generally as a rotary valve which works in conjunction with distributors located between the adsorbent sub-beds. The rotary valve accomplishes moving the input and output locations through first directing the stream introduction or withdrawal lines to specific distributors located between the adsorbent sub-beds. After a specified time period, called the step time, the rotary valve advances one index and redirects the inputs and outputs to the distributors immediately adjacent and downstream for countercurrent flow, or upstream for cocurrent flow, of the previously used distributors. Each advancement of the rotary valve to a new valve position is generally called a valve step, and the completion of all the valve steps is called a valve cycle. The step time is uniform for each valve step in a valve cycle, and ranges generally from about 10 to about 60 minutes. A typical process contains from 4 to 24 adsorbent sub-beds and an equal number of distributors located between each adsorbent sub-bed.

For liquid phase operation, the alkanes, alkenes and alkynes in the solutions to be separated must be liquid at the temperatures of operation, about 30° to about 80° C., and the pressures of operation should be sufficient to maintain the liquid phase. Generally hydrocarbons containing from about 4 to about 18 carbon atoms meet this requirement. The preferred hydrocarbons contain from about 6 to about 17 carbon atoms, and the most preferred hydrocarbons contain from about 9 to about 15 carbon atoms. The branched hydrocarbons may contain one or more branching groups. Alternatively, other hydrocarbons may be used provided they are liquid in the separation process. For example, the desorbent and other components in the mixture may act as a solvent for hydrocarbons which may not otherwise be liquid under operating conditions. Additionally, it is contemplated that the invention may be performed in the gas phase. For gas phase operation, suitable hydrocarbons must have boiling points less than the temperature of operation.

For the liquid phase application, the desorbent, a liquid capable of displacing the adsorbed components, is preferably an alkane. The ability to use an alkane as the desorbent is a significant advantage of the invention since saturated hydrocarbons are generally less hazardous to the environment than typical currently used desorbents such as unsaturated hydrocarbons or ketones. To be used as a desorbent in this application, the alkane must be liquid at the process operating temperatures and pressures. Typical alkanes which are liquid at these temperatures and pressures are those which have from about 4 to about 18 carbon atoms. The structure of the alkane desorbent may be linear, branched, or cyclic. Linear alkane desorbents are preferred, and the most preferred are the alkanes most different in boiling point from the hydrocarbons to be separated. The different boiling point of the desorbent as compared to the hydrocarbons being separated provides for simplified recovery of the separated hydrocarbons from the desorbent. Preferred desorbents include linear alkanes containing from about 4 to about 12 carbon atoms. Alkenes and mixtures of alkanes and alkenes may also serve as liquid phase desorbents, especially when linear and branched alkenes are the hydrocarbons being separated. Preferred alkenes include linear alkenes containing from about 4 to about 12 carbon atoms. For the gas phase application, the desorbent may be hydrogen, nitrogen or helium.

The example below is not intended as a limitation on the scope of the present invention, and is merely illustrative of adsorbent performance. The example employed the commonly used pulse test which is used to evaluate various adsorbents with particular hydrocarbon solutions and desorbents to measure adsorption characteristics. The apparatus for this test consisted of an adsorbent chamber of approximately 5 cc volume having inlet and outlet portions at opposite ends of the chamber. The chamber was contained within a temperature control means and pressure control equipment was used to operate the chamber at a constant predetermined pressure. Analytical instrumentation was attached to the outlet line of the chamber to measure one or more components eluting from the chamber. To perform the test, the adsorbent was placed in the chamber and filled to equilibrium with the desorbent by passing the desorbent through the adsorbent chamber at approximately one linear space velocity. At a convenient time, a 5 µL pulse of the solution to be separated was injected, and then the desorbent flow was resumed. The components were eluted as in a liquid-solid chromatographic operation, and could be analyzed on-line, or samples could be periodically collected and analyzed separately. Adsorbent performance may be rated from the results of this test. The pulse test described above, and used in the example, is a reduced scale of the commonly used pulse test described in U.S. Pat. Nos. 5,220,102 and 3,855,333.

EXAMPLE 1

Separation of Linear and Branched Alkanes Using Ethylene-Bridged Polysilsesquioxane Adsorbent A pulse test, as described above, was performed using an adsorbent chamber, having inlet and outlet portions at opposite ends, which contained 5 cc of ethylene-bridged polysilsesquioxane. The chamber was contained within a temperature control means to keep the temperature of the chamber at 60° C., and pressure control equipment was used to operate the chamber at a constant pressure of 500 psi. An on-line gas chromatograph was used to determine the components of the effluent stream leaving the adsorbent chamber. Desorbent, n-octane, was passed through the adsorbent material at a flow rate of approximately one linear space velocity. At a particular time after equilibrium had been established, a 5 µL pulse of the solution to be separated, a mixture of 2-methylbutane, n-decane, 1-decene, and ethylbenzene was injected. Desorbent flow was resumed, and the effluent was analyzed periodically by the on-line gas chromatograph. As FIG. 1 illustrates, the n-decane eluted first and the 2-methylbutane eluted shortly thereafter. The presence of 1-decene and ethylbenzene is not relevant to applicant's invention and the compounds are not shown in FIG. 1. With optimization of the conditions, applicant believes the separation of the linear and branched components would become more significant.

EXAMPLE 2

Figure 2:
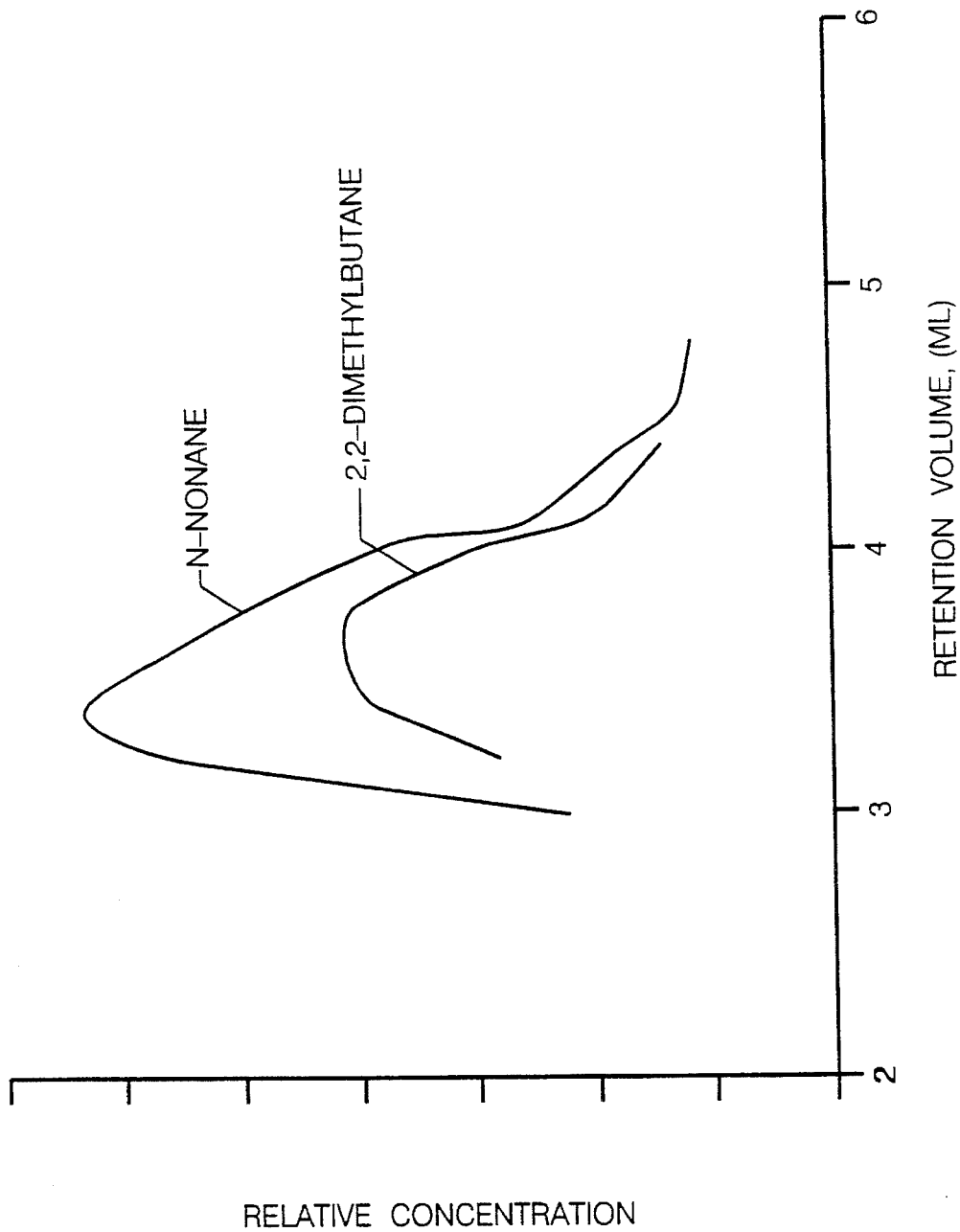
FIG. 2 is the chromatographic plot of the separation of a mixture of a linear alkane and a branched alkane using ethylene-bridged polysilsesquioxane as the adsorbent as conducted in Example 2.

Separation of Linear and Branched Alkanes Using Ethylene-Bridged Polysilsesquioxane Adsorbent A pulse test, as described above, was performed using an adsorbent chamber, having inlet and outlet portions at opposite ends, which contained 5 cc of ethylene-bridged polysilsesquioxane. The chamber was contained within a temperature control means to keep the temperature of the chamber at 60° C., and pressure control equipment was used to operate the chamber at a constant pressure of 500 psi. An on-line gas chromatograph was used to determine the components of the effluent stream leaving the adsorbent chamber. Desorbent, n-octane, was passed through the adsorbent material at a flow rate of approximately one linear space velocity. At a particular time after equilibrium had been established, a 5 µL pulse of the solution to be separated, a mixture of 2,2-dimethylbutane, n-nonane, benzene, toluene, para-xylene, and cumene was injected. Desorbent flow was resumed, and the effluent was analyzed periodically by the on-line gas chromatograph. As FIG. 2 illustrates, the n-nonane eluted first and the 2-methylbutane eluted shortly thereafter. The presence of benzene, toluene, para-xylene, and cumene is not relevant to applicant's invention and the compounds are not shown in FIG. 2. With optimization of the conditions, applicant believes the slight separation of the linear n-nonane and the branched 2,2-dimethylbutane would become more significant.

EXAMPLE 3

Figure 3:
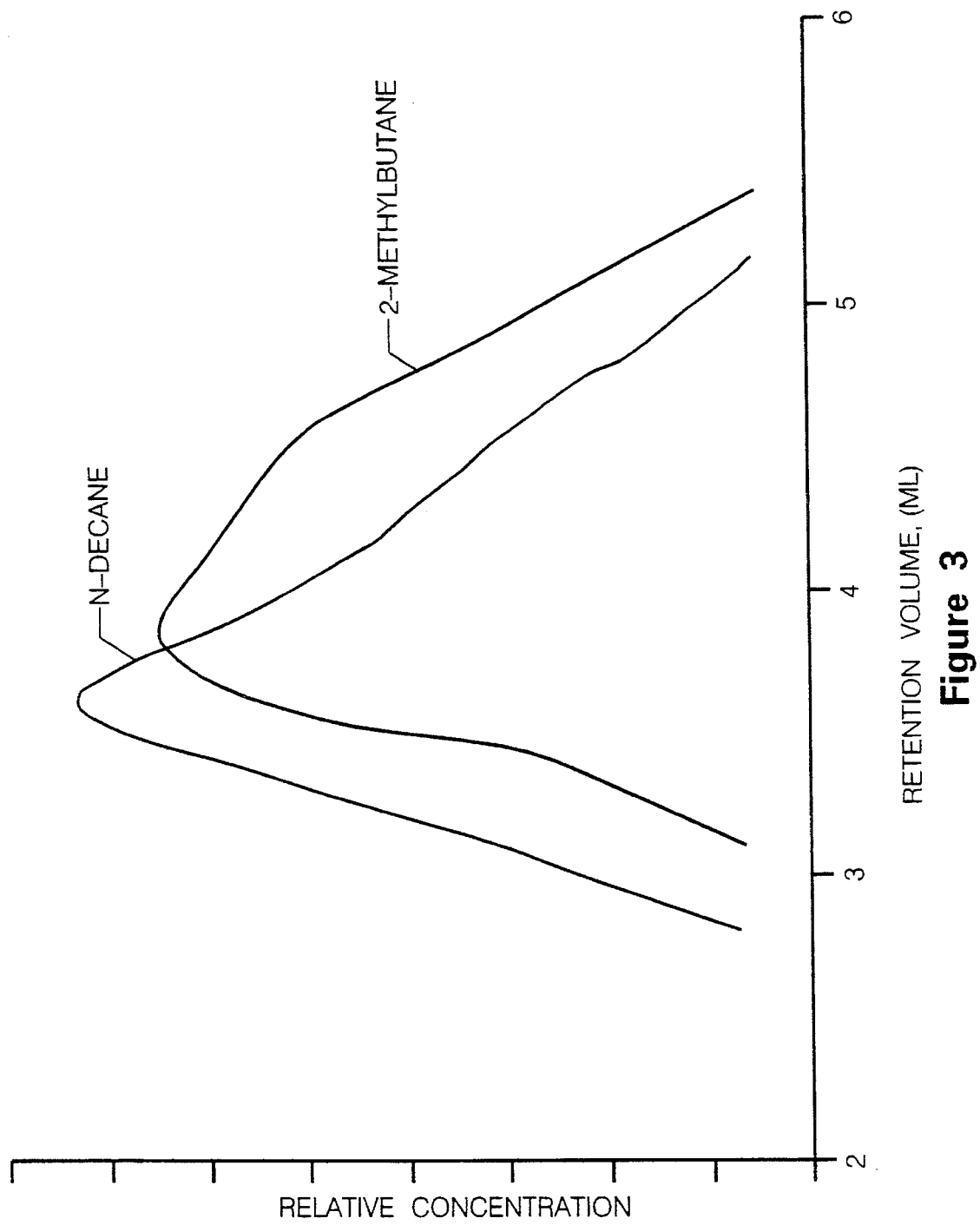
FIG. 3 is the chromatographic plot of the separation of a mixture of a linear alkane and a branched alkane using hexamethylene-bridged polysilsesquioxane as the adsorbent as conducted in Example 3.

Separation of Linear and Branched Alkanes Using Hexamethylene-Bridged Polysilsesquioxane Adsorbent A pulse test, as described above, was performed using an adsorbent chamber, having inlet and outlet portions at opposite ends, which contained 5 cc of hexamethylene-bridged polysilsesquioxane. The chamber was contained within a temperature control means to keep the temperature of the chamber at 60° C., and pressure control equipment was used to operate the chamber at a constant pressure of 500 psi. An on-line gas chromatograph was used to determine the components of the effluent stream leaving the adsorbent chamber. Desorbent, n-octane, was passed through the adsorbent material at a flow rate of approximately one linear space velocity. At a particular time after equilibrium had been established, a 5 µL pulse of the solution to be separated, a mixture of 2,2-dimethylbutane, n-decane, 1-decene, and ethylbenzene was injected. Desorbent flow was resumed, and the effluent was analyzed periodically by the on-line gas chromatograph. As FIG. 3 illustrates, the n-decane eluted first and the 2-methylbutane eluted shortly thereafter. The presence of 1-decene and ethylbenzene is not relevant to applicant's invention and the compounds are not shown in FIG. 3. With optimization of the conditions, applicant believes the separation of the linear and branched components would become more significant.

What is claimed is:

1. A process for separating the components of a solution which is (1) a mixture of linear and branched alkanes, or (2) a mixture of linear and branched alkenes, or (3) a mixture of linear and branched alkynes, into a linear hydrocarbon portion and a branched hydrocarbon portion, comprising:

a. contacting said solution with an alkylene-bridged polysilsesquioxane adsorbent where said alkylene-bridging group contains from about 2 to about 14 carbon atoms, said adsorbent effective to adsorb hydrocarbons with increasing strength in the order of linear hydrocarbons< branched hydrocarbons;

b. desorbing the adsorbed linear hydrocarbons from said adsorbent using a desorbent and collecting the desorbed linear hydrocarbons; and c. desorbing the adsorbed branched hydrocarbons from said adsorbent using the desorbent and collecting the desorbed branched hydrocarbons.

2. The process of claim 1 where said alkylene-bridging group is ethylene.

3. The process of claim 1 where said process is operated in the simulated moving bed mode.

4. The process of claim 1 where the process is operated in a fixed bed mode.

5. The process of claim 1 where said process is operated in the liquid phase.

6. The process of claim 5 where the desorbent is an alkane.

7. The process of claim 5 where the desorbent is selected from the group consisting of linear alkanes containing from about 4 to about 12 carbon atoms.

8. The process of claim 1 where said process is operated in the gas phase.

9. The process of claim 8 where the desorbent is selected from the group consisting of hydrogen, nitrogen and helium.

\* \* \* \* \*